United States Patent [19]

Ganslaw et al.

[11] 4,043,952

[45] Aug. 23, 1977

[54] SURFACE TREATMENT PROCESS FOR IMPROVING DISPERSIBILITY OF AN ABSORBENT COMPOSITION, AND PRODUCT THEREOF

[75] Inventors: Stuart H. Ganslaw, Piscataway; Howard G. Katz, East Windsor, both of N.J.

[73] Assignee: National Starch and Chemical Corporation, Bridgewater, N.J.

[21] Appl. No.: 576,132

[22] Filed: May 9, 1975

[51] Int. Cl.$^2$ ................................................. C08L 3/04
[52] U.S. Cl. ........................... 260/17.4 ST; 252/410; 260/79; 260/79.7; 260/117; 260/119; 260/123.5; 526/47; 526/48; 536/1; 536/3; 536/56; 536/59; 536/62; 536/63; 536/101; 536/105; 536/111; 536/114; 536/121
[58] Field of Search ................. 260/79, 17.4 ST, 79.7, 260/117, 119, 123.5, 209.6, 209 R, 215, 218, 219, 231 CM, 233.3 A, 233.3 R, 233.5; 526/47, 48; 536/1, 3, 56, 59, 62, 63, 101, 105, 111, 114, 121; 252/410

[56] References Cited

U.S. PATENT DOCUMENTS

| 3,267,083 | 8/1966 | Imhof | 526/47 |
|---|---|---|---|
| 3,328,892 | 7/1967 | Man | 34/9 |
| 3,355,319 | 11/1967 | Rees | 526/48 |
| 3,493,550 | 2/1970 | Schmitt et al. | 526/48 |
| 3,586,659 | 6/1971 | Hay et al. | 526/47 |
| 3,740,366 | 6/1973 | Sanderson et al. | 526/48 |
| 3,769,254 | 10/1973 | Anderson et al. | 526/47 |
| 3,779,952 | 12/1973 | Leonard, Jr. | 526/48 |
| 3,802,912 | 4/1974 | Otocka | 526/48 |
| 3,850,898 | 11/1974 | Ide et al. | 526/47 |
| 3,920,605 | 11/1975 | Sato et al. | 526/47 |

OTHER PUBLICATIONS

McGraw-Hill, Encyclopedia of Science and Technology, vol. 14, 1971, pp. 52 and 53.
Periodic Table of the Elements, E. H. Sargent and Co., 1962.

*Primary Examiner*—Melvyn I. Marquis
*Attorney, Agent, or Firm*—James & Franklin

[57] ABSTRACT

The aqueous dispersibility of a water-absorbent composition of matter is improved by a surface treatment which ionically complexes the surface thereof to a moderate degree. A dispersion is formed comprising a water-absorbent composition of matter based on an anionic poly-electrolyte, at least one polyvalent metal cation, and a dispersing medium in which the composition of matter is substantially insoluble. The dispersion is maintained within a given temperature range for a period of time sufficient to ionically complex the exposed surface of the composition of matter, and the dispersing medium is then removed. The product is characterized by a linkage density which is greater at the surface thereof than in the interior thereof and by the presence of ionic linkages at the surface thereof.

19 Claims, No Drawings

SURFACE TREATMENT PROCESS FOR IMPROVING DISPERSIBILITY OF AN ABSORBENT COMPOSITION, AND PRODUCT THEREOF

BACKGROUND OF THE INVENTION

The present invention relates in general to a method of surface treating a water-absorbent composition of matter to improve its water dispersibility and to reduce its lumping tendencies, and the dry water-absorbent compositions produced thereby.

Absorbent compositions of matter based on anionic poly-electrolytes generally fall into three classes. The first class consists of the substantially water-soluble hydrocolloid materials long known in the art. Such materials merely increase the viscosity of (i.e., thicken) the liquid exposed thereto; in the presence of an added liquid excess, such materials lose their power to retain the viscosity they previously achieved. Nonetheless, such water-soluble materials are useful in a number of applications where they will be exposed to only a controlled amount of fluid; for example, as adhesives, thickeners, coatings, textile sizing agents, water treatment and purification agents, drainage aids, etc.

More recently, there has been a high degree of activity in the area of water-insoluble particulate hydrocolloid absorbent compositions of matter and products using the same, such as absorbent dressings, diapers, catamenial tampons, and the like for absorbing aqueous fluids such as water, urine and other aqueous body exudates. Such substantially water-insoluble compounds maintain their particular character as they imbibe and absorb many times their weight of surrounding liquid, and in doing so, swell. The compounds are capable of absorbing at least 15 times their weight of fluid. In doing so, each individual absorbent particle swells or enlarges several hundred percent times its individual parameter without destruction of its initial particulate integrity. Each particle maintains the approximate shape and geometry it had before contact with liquid, but the dimensions are greatly enlarged to provide for the binding of the liquid absorbed therein. As the water-insoluble compound accepts liquid, it substantially immobilizes the liquid therein, and the resulting particulate liquid-swollen structure is gelatinous. The mass of swollen particulate water-insoluble particles defines an aciniform structure since each individual absorbent particle is a greatly enlarged particle, having become liquid-swollen or grape-like or acinus in form due to the liquid it has absorbed. The individual swollen particles are tacky and hence form a clustered mass of liquid-swollen particles. The particles remain in an acinus form state despite the presence of liquid in excess of their ability to absorb. The liquid-swollen particles bind their absorbed water tightly, but upon drying, they become dehydrated and return more or less to their original size. At this time they can operate more or less as before to absorb and bind liquids.

The water-insoluble absorbent compositions described above are generally formed in either of two ways (corresponding to the second and third classes). As described in U.S. Pat. NOs. 3,628,534; 3,669,103; and 3,670,731; one or more monomers, which if homopolymerized would form a water-soluble polymer, are copolymerized with a monomer which covalently crosslinks the molecule and introduces a limited water-insolubility. In general, the degree of crosslinking is contained so that the polymer network of the hydrocolloid is not soluble in aqueous media, yet remains flexible and swells as the aqueous media is absorbed within its structure.

Alternately, as described in the U.S. patent application Ser. No. 556,291, filed Mar. 7, 1975, such water-insoluble compositions may be formed through the polymerization and ionic complexing of one or more monomers, which if homopolymerized would form a water-soluble polymer, with polyvalent metal cations having a valance of at least three. The advantage of the ionic complex compositions over the covalently cross-linked compositions is that the former are easy to shape and apply to substrates for particular applications since they may be uncomplexed at an elevated pH and re-complexed at a lower pH.

Regardless of the relative merits and demerits of the three classes of water-absorbent compositions of matter, all are subject to the same problem variously termed in the art as lumping, poor "wet-out" or poor water dispersibility.

Upon exposure to the aqueous fluid to be absorbed, the absorbent compositions exhibit poor dispersibility in the aqueous medium and at least initially, form visible clumps consisting of fluid-swollen material on the surface and relatively dry material on the inside. Especially when used in the form of relatively fine powders, the exposed surface of the absorbent composition forms a gel-like structure which inhibits the passage of the aqueous fluid therethrough. Accordingly, the absorbent capacity of the compositions is at least initially reflective of only the absorbent capacity of the surface, and not the absorbent capacity of the interior as well. A slow rate of exposure of the absorbent composition to the aqueous medium to be absorbed, the use of relatively large granules of the absorbent composition, and agitation of the aqueous medium during exposure tend to reduce the occurrence of lumping, while agitation of the aqueous medium after exposure and the passage of time tend to dissolve lumping once it has occurred. Nonetheless, in many instances the specific application in which the absorbent composition is used precludes resort to one or more of the aforementioned expediencies, and the need remains for an absorbent composition having improved aqueous dispersibility (i.e., better wet-out and less lumping).

One object of the present invention is to provide a process for improving the aqueous dispersibility or wet-out of an absorbent composition based on an anionic poly-electrolyte.

Another object is to provide such a process which is effective with water-soluble compositions, covalently crosslinked water-insoluble compositions and ionically complexed water-insoluble compositions.

A further object to provide such a process which reduces the amount of lumping exhibited by the absorbent composition upon rapid exposure thereof to large quantities of the aqueous fluid to be absorbed.

Stll another object is to provide such a process which enables the absorbent composition to reach full dispersion in the aqueous fluid to be absorbed in a reduced period of time.

A final object is to provide an absorbent composition treated according to such a process.

SUMMARY OF THE INVENTION

It has now been found that the aqueous dispersibility or wet-out of a water-absorbent composition of matter based on an anionic poly-electrolyte may be improved by a surface treatment which ionically complexes the exposed surface of the absorbent composition. The ionic complexing of the surface is believed to retard the formation of a surface gel which inhibits the passage of aqueous fluid into the interior of the absorbent composition. Thus, even upon rapid exposure to large quantities of the aqueous fluid, the full capacity of the absorbent composition to imbibe the aqueous fluid is rapidly realized, the imbibing of the aqueous fluid by the interior aiding in the dispersion of the absorbent composition into the aqueous fluid thereabout.

The surface treatment process involves forming a dispersion comprising a water-absorbent composition of matter based on an anionic poly-electrolyte, at least one polyvalent metal cation, and a dispersing medium in which the composition of matter is substantially insoluble. The dispersion is maintained at a temperature of about −40° C to about +150° C for a period of time sufficient for the cation to ionically complex the exposed surface of the composition of matter. Thereafter, the solvent is removed from the dispersion, leaving the modified aqueous-dispersible absorbent composition of matter.

The absorbent composition of matter may be any of the three classes previously described: (1) a water-soluble anionic poly-electrolyte, (2) a water-swellable, water-insoluble covalently crosslinked anionic poly-electrolyte, or (3) a water-swellable, water-insoluble ionic complex of a water-soluble anionic poly-electrolyte and a polyvalent metal cation having a valence of at least three. The polyvalent metal cation with which the absorbent composition of matter described above is treated is generally selected from the group consisting of the ions of metals of Groups IIA–VIA, IB–IIB, and VIII of the Periodic Table. The dispersing medium is generally selected from the group consisting of aliphatic and aromatic alcohols containing 1–18 carbon atoms, aliphatic and aromatic esters, ketones, alkyl ethers, alkanes containing 5–18 carbon atoms, aromatics, and blends of water-miscible solvents with water. Typically the dispersion comprises, per gram of the absorbent composition of matter on a dry basis, about 0.5–100 gms. of dispersing medium and about 0.05–10.0 milliequivalents of cation.

In a preferred embodiment the dispersion comprises, per gram of the absorbent composition of matter on a dry basis, about 2–10 grams of dispersing medium and about 0.1–2.0 milliequivalents of cation. The dispersion is maintained at the aforesaid temperature for at least a minute, and preferably at a temperature of about 25°–110° C for about 5–60 minutes to insure ionic complexing of the exposed surface of the absorbent composition of matter.

The water-dispersible water-absorbent particles produced by the surface treatment process are characterized by a linkage density at the particle surface greater than the linkage density in the particle interior. The linkages at the particle surface comprise at least in part ionic complexing of the anionic poly-electrolyte by polyvalent metal cations, such as may be achieved by the process of the present invention.

DETAILED DESCRIPTION OF THE PREFERRED EMBODIMENTS

The initial step of the surface treatment process is the formation of a dispersion comprising a water-absorbent composition of matter based on an anionic poly-electrolyte, at least one polyvalent metal cation, and a dispersing medium in which the composition of matter is substantially insoluble. Each of these will now be discussed in turn below.

THE WATER-ABSORBENT COMPOSITION

The three classes of water-absorbent compositions are the water-soluble compositions, the covalently crosslinked water-insoluble compositions, and the ionically complexed water-insoluble compositions.

The absorbent compositions of matter of the first class (water-soluble) are poly-electrolytes comprising natural or synthetic polymers characterized by substantial water-solubility in an aqueous medium and by the presence of anionic groups (preferably carboxyl, sulfonate, sulfate or phosphate anionic groups). The preferred natural polymers are the anionic derivatives of starch or cellulose, and the preferred synthetic polymers are the carboxylic acid homopolymers or copolymers containing at least 20 mole percent carboxylic acid units, e.g., polyacrylic acid.

Exemplary of the carboxylic acid-containing poly-electrolytes are the synthetic copolymers of ethylenically unsaturated monomers with mono-ethylenically unsaturated carboxylic acids or their partially neutralized salts. Examples of the preferred $\alpha,\beta$-mono-unsaturated carboxylic acids include acrylic acid, methacrylic acid, maleic acid, maleic anhydride, itaconic acid, itaconic anhydride, fumaric acid, half esters or half amides of maleic, fumaric and itaconic acid, crotonic acid, etc. Examples of the preferred $\alpha,\beta$-ethylenically unsaturated monomers include acrylamide or methacrylamide and their N and N, N dialkyl derivatives containing 1–18 carbon alkyl groups, alkyl acrylates and methacrylates containing 1–18 carbon alkyl groups, vinyl esters, vinyl aromatic compounds, dienes, etc.

Homopolymers of monoethylenically unsaturated carboxylic acids or mixtures of these monomers may also be used. Examples include acrylic and methacrylic acid homopolymers and acrylic acid/methacrylic acid copolymers.

Exemplary of the sulfonic acid-containing poly-electrolytes are the homopolymers of monoethylenically unsaturated sulfonic acids (or salts thereof) and copolymers thereof with the aforementioned ethylenically unsaturated monomers. Suitable sulfonate-containing monomers include aromatic sulfonic acids (such as styrene sulfonic acids, 2-vinyl-3-bromobenzenesulfonic acid, 2-vinyl-4-ethylbenzenesulfonic acid, 2-allyl benzene sulfonic acid, vinylphenylmethane-sulfonic acid and 1-sulfo-3-vinylphenylmethane sulfonic acid), heterocyclic sulfonic acids (such as 2-sulfo-4-vinylfurane and 2-sulfo-5-allylfurane), aliphatic sulfonic acids (such as ethylenesulfonic acid and 1-phenylethylene sulfonic acid), sulfonic acids containing more than a single acid radical (such as $\alpha$-sulfoacrylic acid and $\alpha$-sulfoethylenesulfonic acid), and sulfonic acid derivatives hydrolizable to the acid form (such as alkenyl sulfonic acid compounds and sulfoalkylacrylate compounds).

Exemplary of the sulfate-containing poly-electrolytes are those formed by reacting homopolymers and copolymers containing hydroxyl groups or residual polymer unsaturation with sulfur trioxide or sulfuric acid; for example, sulfated polyvinyl alcohol, sulfated hydroxyethyl acrylate, sulfated hydroxypropyl methacrylate. Exemplary of the phosphate-containing poly-electrolytes are the homopolymers and copolymers of ethylenically unsaturated monomers containing a phosphoric acid moiety, such as methacryloxy ethyl phosphate.

Exemplary of the poly-electrolytes formed of natural polymers and their derivatives are the carboxylated, sulfonated, sulfated, and phosphated derivatives of cellulose and starch, such as carboxymethyl cellulose and carboxymethyl starch. Naturally occurring anionic poly-electrolytes such as alginates, carrageenen, proteins (such as gelatin, casein, and soya protein), gum arabic, algin, agar, gum chati also have utility.

The poly-electrolyte polymers may be prepared by conventional polymerization techniques, such as solution, emulsion, suspension, and precipitation polymerization techniques. While the polymers are preferably prepared using a free radical polymerization mechanism, other polymerization mechanisms, including anionic and cationic mechanisms, may be used. The poly-electrolyte generally has a molecular weight of from 10,000 to 10,000,000.

The absorbent composition of matter of the second class (water-insoluble covalently-crosslinked) may be formed from anionic poly-electrolytes of the first class which have been covalently crosslinked to render them water insoluble, yet water-swellable. Such water-insoluble absorbent compositions and their preparation are described in detail in the aforementioned U.S. Pat. Nos. 3,628,534, 3,669,103 and 3,670,731. Typically polyfunctional compounds, such as divinyl benzene, are copolymerized with the poly-electrolyte monomer or pre-polymer so as to enter into a plurality of poly-electrolyte polymer chains or attach to the available dependent functional groups of a plurality of polymer chains. Conventional polymerization techniques including ultraviolet and other radiation initiated polymerization mechanisms, may be used. Examples of suitable polyfunctional compounds include divinyl compounds (such as divinyl benzene, divinyl diethylene glycol diether, divinyl diphenyl silane and divinyl sulfone), allyl compounds (such as triallyl cyanurate, trimethylol propane diallyl ether, allyl methacrylate, allyl acrylate, allyl crotonate, diallyl phthalate, diallyl succinate and diallyl sucrose), polyfunctional acrylates and methacrylates (such as tetraethylene glycol diacrylate, triethylene glycol dimethacrylate, pentaerythritol tetra-acrylate, ethylidene dimethacrylate, and trimethylol propane trimethacrylate), and polyfunctional acrylamides and methacrylamides (such as N, N'-methylene bis-acrylamide, and N, N'-methylene bis-methacrylamide, etc.).

An absorbent composition of this second class (like one of the third class described hereinbelow) is defined as providing a gelatinous agglomerate of liquid-swollen particulate members in the presence of a quantity of body exudate, as capable of absorbing at least about fifteen times its weight in body exudate, and as capable of retaining the absorbed exudate when exposed to pressure sufficient to deform the agglomerate.

The absorbent compositions of the third class (water-insoluble ionically complexed) may be formed from anionic poly-electrolytes of the first class which have been ionically complexed to render them water-insoluble, yet water-swellable. A polyvalent metal cation is used to complex the poly-electrolyte to render the overall polymer composite substantially insoluble yet highly swellable in aqueous media such as water, urine, blood, etc. The cations have a valence of at least three and are cations of metals belonging to the following groups of the Periodic Table: IIIB, IVB, VB, VIB, VIIB, VIII, IIIA, IVA, VA, VIA. The preferred metals are aluminum, zirconium, chromium, titanium, and iron, and to a lesser degree antimony and bismuth. Aluminum is an especially preferred metal.

The metal compound used to contribute the cation can be added prior to polymerization of the monomers of the poly-electrolyte, during polymerization or post-added to a polymeric polyelectrolyte solution, the only restraint being that the poly-electrolyte compound be at least ionizable or soluble in the system. The polyvalent metal can be added to the composition by means of a basic, acidic or neutral salt, hydroxide, oxide or other compound or complex which has at least limited solubility in water or an organic solvent in which the poly-electrolyte and its constituent monomers are also soluble at the time of cation introduction.

Examples of inorganic salts include chlorides, nitrates, sulfates, borates, bromides, iodines, fluorides, nitrides, perchlorates, phosphates, and sulfides, such as aluminum chloride, aluminum sulfate, ferric sulfate, ferric nitrate, antimony trichloride, bismuth chloride, zirconium chloride, chromic sulfate, and chromic nitrate. Examples of organic salts include salts of carboxylic acids such as carbonates, formates, acetates, butyrates, hexanoates, adipates, citrates, lactates, oxalates, oleates, propionates, salicylates, glycinates, glycollates and tartrates; for example, aluminum formoacetate, basic aluminum acetate, chromic acetate, aluminum citrate, aluminum diformate, aluminum triformate, titanium oxalate, ferric acetate, aluminum octate, ferric oleate, zirconium lactate and zirconium acetate.

The ammonia and amine complexes (and especially those coordinated with ammonia) of these metals are particularly useful. Amines capable of so complexing include morpholine, monoethanol amine, diethylaminoethanol and ethylenediamine. Examples of these amine complexes include ammonium zirconyl carbonate, ammonium zirconyl glycinate, and ammonium zirconium chelate of nitrilotriacetic acid. Polyvalent metal complexes (salts) of organic acids that are capable of solubilization in an alkaline pH range may also be employed. Such anions as acetate, glutamate, formate, carbonate, salicylate, glycollate, octoate, benzoate, gloconate, oxalate and lactate are satisfactory. Polyvalent metal chelates wherein the ligand is a bidentate amino acid, such as glycine or alanine, are particularly useful.

Other organic compounds containing polyvalent metals are also useful; for example, the metal alkoxides, metal alkyls, and acetyl acetonates, such as aluminum isopropoxide, titanium acetyl acetonate, aluminum acetyl acetonate, chromic acetyl acetonate, zirconium ethoxide, chromic isobutoxide and triethyl aluminum.

The cations of one or more of such metals are present in the absorbent composition at a level of 0.01–5.0 milliequivalents of cation per gram of poly-electrolyte, and preferably 0.1–1.0 milliequivalents of cation per gram of poly-electrolyte. Lower cation levels do not render the polymeric composition water-insoluble, while higher cation levels render the polymer composition not only water-insoluble, but also non-swellable.

Lower cation levels within the range are especially effective when the poly-electrolyte is of relatively high molecular weight. Regardless of pH, higher cation levels within the specified range contribute to the permanency of the gel formed by exposure of the dried complex to the fluid to be absorbed; but it is noted that in many applications (e.g., diapers, tampons, etc.) a gel life of only a few hours is required and hence lower cations levels within the specified range may be suitable. In general it has been found that the optimum cation level varies with the ion size of the cation.

As will be recognized by those familiar with the art of complexing, not all of the available ionic linkages of a given polyvalent cation will necessarily be associated with different poly-electrolyte polymeric chains; especially in the case of the cations, such as zirconium, having valence or oxidation states greater than 3, inner salt formation (that is, the attachment of a single cation exclusively to a single polymer chain or to a number of polymer chains less than the valence) will occur to an unspecified degree dependent on the spatial geometries presented by the reagents involved, relative concentrations, etc. Accordingly, the specification herein of the relationship of milliequivalent weights of cation per gram of poly-electrolyte is predicated not on a theoretical basis, but rather on experimental results.

The absorbency of the composition is improved when the poly-electrolyte is at higher molecular weight levels within the specified range of 10,000 to 10,000,000. Accordingly, various di-functional monomers such as allyl methacrylate may be used to chain extend the poly-electrolyte prior to exposure to the cation. The amount of chain extender used must, of course, not render the poly-electrolyte insoluble in aqueous media. The increased chain length of the poly-electrolyte permits lower cation levels to be employed as there are fewer polymer chains to be complexed.

The absorbency of the composition is also improved when the poly-electrolyte has up to about 95%, preferably 40-85%, of its anionic groups neutralized with a suitable base such as an alkali metal hydroxide, as primary, secondary or tertiary amine, etc. The neutralization acts to uncoil and straighten out the polymer chains in aqueous fluids so that the final complex is more swellable in the presence of such fluids.

The poly-electrolytes must be substantially water-soluble at some pH between 2.0 and 8.5 to utilize the metal complexing and form the desired water-insoluble absorbent complex. However, the reversibility of ionic complexing (as opposed to covalent bonding) is well known in the chemical art and once the pH of the complex is raised above a certain level (i.e., the pH of reversibility), the complex breaks down, yielding again the water-soluble non-absorbent poly-electrolyte. This reversibility of complex formation facilitates easy and economical application of the complex onto a desired substrate by use of conventional fluid application techniques. Prior to application a suitable quantity of a base is added to the complex to cause dissolution thereof into a solution containing the cation and the water-soluble poly-electrolyte thereof, and subsequent to application an acid is added to the solution to cause a re-formation of the absorbent complex. In a preferred technique a volatile base (such as ammonium hydroxide) is employed to break the complex so that a mere drying of the solution suffices to lower the pH and hence cause re-formation of the absorbent complex without the addition of an acid. The acid strength of the poly-electrolyte acid has a marked effect upon the pH of reversibility. The higher the acid strength (i.e., the lower the pH of dissociation), the lower the pH of reversibility. For example, polyacrylic acid, a weak polymeric acid, reverses its complex at pH 8.5-9.0 whereas styrene sulfonic acid, a very strong polymeric acid, reverses its complex at a pH of about 3.5-5.0.

The preferred composition is a polyacrylic acid-/aluminum cation complex. The aluminum cation is typically added (as aluminum acetate) during precipitation polymerization of the acrylic acid with a free radical catalyst, to provide about 0.3 milliequivalents of aluminum per gram of polymer, according to the following formulation:

| Parts by Weights | Ingredients |
|---|---|
| 73.07 | potassium acrylate |
| 27.74 | acrylic acid |
| 0.19 | allyl methacrylate |
| 1.49 | basic aluminum acetate |

In both the second and third classes of absorbent compositions (the water-insoluble ones), the formation of a light-to-moderate network of linkages between polymer chains — in one case covalent linkages and in the other case ionic linkages — renders the composition water-insoluble, but water-swellable. The dry absorbent composition is rendered, in the presence of a quantity of body exudate or other water-containing material into a gelatinous agglomerate of liquid-swollen particulate members. The composition is capable of absorbing at least 15 times its weight in body exudate, and generally at least 40 times its weight. Furthermore, the composition is capable of retaining the absorbed exudate even when exposed to pressure sufficient to deform the agglomerate, and generally up to pressures of about 2.5 psi.

The absorbent capacity of the composition is independent of its physical dry form, and accordingly the composition may be used as a film, powder, or fiber. It can be utilized as an absorbent of any aqueous fluid mixture such as water, blood or urine, and is useful in conjunction with other materials to form articles of manufacture (such as absorbent dressings, diapers, sanitary napkins, catamenial tampons, cosmetics, absorbent non-woven fabrics, and the like) as well as by itself (as an absorbent body powder, soil additive to maintain moisture, anti-perspirant, seed germination aid, pet litter additive to absorb urine, and the like). The composition may be utilized furthermore in articles of manufacture where water absorbency is not the end in and of itself, but merely a means to the end; for example, the absorbent composition may be an ingredient of tablets designed to dissolve rapidly in water or bodily fluids.

THE POLYVALENT METAL CATION

The polyvalent metal cations useful in the surface treatment process of the present invention have a valence of at least two and are cations of metals belonging to the following groups of the Periodic Table: IB, IIB, IIIB, IVB, VB, VIB, VIIB, VIII, IIA, IIIA, IVA, VA, VIA. The preferred metals are aluminum, zirconium, chromium, titanium and zinc. Aluminum is an especially preferred metal.

The polyvalent metal compound providing the polyvalent metal cation can be added to the dispersing medium before, with or after the absorbent composition of matter. The only restraint on selection of the polyvalent metal compound is that it must be at least ionizable or soluble in the dispersing medium. Thus the polyvalent metal cations can be added to the dispersing medium by means of a basic, acidic or neutral salt, hydroxide, oxide or other compound or complex which has at least limited solubility in the dispersing medium.

Examples of suitable inorganic salts include chlorides, nitrates, sulfates, borates, bromides, iodines, fluorides, nitrides, perchlorates, phosphates, and sulfides, such as zinc chloride, barium chloride, aluminum chloride, aluminum sulfate, ferric sulfate, ferric nitrate, antimony trichloride, bismuth chloride, zirconium chloride, chromic sulfate, and chromic nitrate. Examples of suitable organic salts include salts of carboxylic acids such as carbonates, formates, acetates, butyrates, hexanoates, adipates, citrates, lactates, oxalates, oleates, propionates, salicylates, glycinates, glycollates and tartrates; for example, zinc acetate, chromium acetate, aluminum formoacetate, basic aluminum acetate, chromic acetate, aluminum citrate, aluminum diformate, aluminum triformate, titanium oxalate, ferric acetate, aluminum octate, ferric oleate, zirconium lactate and zirconium acetate. Basic aluminum acetate is a preferred organic salt.

The ammonia and amine complexes (and especially those coordinated with ammonia) of these metals are particularly useful. Amines capable of so complexing include morpholine, monoethanol amine, diethylaminoethanol and ethylenediamine. Examples of these amine complexes include ammonium zirconyl carbonate, ammonium zirconyl glycinate, and ammonium zirconium chelate of nitrilotriacetic acid. Polyvalent metal complexes (salts) or organic acids that are capable of solubilization in the dispersing medium may also be employed. Such anions as acetate, glutamate, formate, carbonate, salicylate, glycollate, octoate, benzoate, gloconate, oxalate and lactate are satisfactory. Polyvalent metal chelates wherein the ligand is a bidentate amino acid, such as glycine or alanine, are particularly useful.

Other organic compounds containing polyvalent metals are also useful; for example, the metal alkoxides, metal alkyls, and acetyl acetonates, such as aluminum isopropoxide, titanium acetyl acetonate, aluminum acetyl acetonate, chromic acetyl acetonate, zirconium ethoxide, chromic isobutoxide and triethyl aluminum.

The cations of one or more of such metals are present in the dispersion at a level of 0.05–10.0 milliequivalents of cation per gram of the absorbent composition of matter on a dry basis, and preferably 0.1–2.0 milliequivalents of cation per gram. In general, the finer the particle form of the dry absorbent composition, the more cation should be employed.

THE DISPERSING MEDIUM

The choice of dispersing medium is not critical, providing only that the absorbent composition of matter is substantially insoluble therein. Of course, as pointed out above, the compound used to introduce the polyvalent metal cation into the dispersion must also be ionizable or soluble in the dispersing medium. The dispersing medium is preferably one or more of the following liquids in which the dry absorbent composition of matter is substantially insoluble: aliphatic or aromatic alcohols containing 1 to 18 carbon atoms (such as methanol, ethanol, isopropanol, 2 ethyl hexanol, benzyl alcohol, etc.), ketones (such as acetone, methyl ethyl ketone, etc.), alkyl ethers (such as ethyl ether, etc.), aliphatic and aromatic esters (such as ethyl acetate, butyl propionate, etc.), alkanes containing 5 to 18 carbon atoms (such as hexane, heptane, etc.), aromatics (such as benzene, toluene, etc.), blends of water-miscible solvents (such as lower alkyl ketones and alcohols, dioxane, dimethyl formamide, etc.) with water. Other solvents such as dimethyl sulfoxide and tetrahydrofuran also have utility.

The dispersing medium is typically (but not necessarily) used at a level of about 0.5 to 100 parts, and preferably about 2–10 parts, per part by weight of the absorbent composition of matter on a dry basis.

TREATMENT OF THE DISPERSION

Once the dispersion is formed, it is maintained for a period of time sufficient to permit the polyvalent metal cation to ionically complex the surface of the absorbent composition of matter (and more particularly the anionic poly-electrolyte thereof). In general, a moderate level of ionic complexing at the surface is desired. If the level of surface complexing is either too light or too heavy, no improvement in water-dispersibility is gained. The optimum level of surface complexing may easily be determined for a given poly-electrolyte and a given cation set by plotting the dispersibility and/or full dispersion time as a function of various levels of surface crosslinking. The amount of time required will naturally depend both upon the degree of complexing desired and the temperature at which the dispersion is maintained. Generally, the temperature is maintained within the range −40° to +150° C, preferably from 25° to 110° C. At these temperatures, suitable complexing is achieved in a period of time from about one minute to several hours, and preferably from five minutes to one hour.

After the desired degree of complexing has occurred, the modified composition and the dispersing medium are separated by conventional techniques, for example, by evaporation of the dispersing medium or by filtration. If desired, the modified composition may be further dried by conventional techniques, such as heating.

The ionic complexing of the surface of the absorbent composition results in particles having a linkage density (i.e., a density of polymer inter-chain linkages — whether ionic or covalent in nature) which is higher at the surface thereof than in the interior thereof. In the case of water-soluble poly-electrolytes, the linkage density in the interior will be zero or very low, and the higher linkage density at the surface almost exclusively or exclusively due to the ionic complexing imparted by the surface treatment. In the case of the water-insoluble water-swellable covalently crosslinked anionic poly-electrolytes, the typically uniform density of covalent linkages in the unmodified composition will be supplemented at the surface of the modified composition by the ionic linkages resulting from the surface treatment process. (In some instances the density of covalent linkages in the unmodified composition may be higher at the surface than in the interior; nonetheless, the presence of the additional linkages at the surface imparted by the surface treatment — i.e., the ionic linkages — will further enhance the dispersibility of the modified composition). In the case of the water-insoluble water-swellable ionic complexes, the uniform density of ionic linkages in the unmodified composition will be supplemented at the surface of the modified composition by the additional ionic linkages resulting from the surface treatment process. In this regard, it is to be noted that the same or different cations may be used in the surface treatment process of the present invention as are already present in the unmodified ionic complex; of course, the range of cations useful in the surface treatment is greater than the range of cations useful in forming the unmodified ionic complex, the latter being limited to cations having a valence of at least three as aforementioned.

In any case, the tendency of the surface of the absorbent composition to rapidly form a relatively water-impermeable gel upon rapid exposure to large quantities of the aqueous medium to be absorbed is inhibited by the surface treatment so that the aqueous medium has an opportunity to enter into the interior of the absorbent composition before the surface thereof has an opportunity to swell and form the gel. The imbibing of the aqueous medium by the interior of the absorbent composition exerts an outward pressure which effects rapid dispersal of the absorbent composition in the aqueous fluid. Thus the process of the present invention is believed to operate on the anomalous principle that a reduction in the rate at which the surface of the absorbent composition imbibes the aqueous fluid will increase the rate at which the interior of the absorbent composition will absorb the aqueous fluid and that, on balance, this sacrifice in surface imbibing rate will increase the overall imbibing rate of the absorbent composition. The data presented below in the examples substantiates this principle by indicating that the absorbent compositions modified by the process of the present invention exhibit both improved initial dispersion upon exposure to the aqueous medium (i.e., less lumping) and also a more rapid complete dispersion within the aqueous medium. Of course, it must also be realized that a very high level of ionic complexing at the surface of the modified composition will also act as a relatively water-impermeable barrier and preclude the desirable entry of aqueous fluid into the interior. However, with the above described operative principle in mind, the practitioner will without undue experimentation be able to finely adjust the moderate degree of surface complexing effected by the process of the present invention to accommodate the needs of a particular application by the selection of appropriate times and temperatures for the complexing reaction and appropriate ratios for the polyvalent metal cation and the absorbent composition of matter within the dispersion.

EXAMPLES

The following examples illustrate the efficacy of the present invention. All parts are by weight unless otherwise specified. Example I illustrates preparation or obtaining of the dry absorbent compositions of matter, Example II illustrates modification of such dry absorbent compositions of matter by the surface treatment process of the present invention, and Example III illustrates the comparative improvements in initial dispersion and dispersion time achieved by the surface treatment process.

EXAMPLE I

Dry absorbent compositions of matter based on anionic poly-electrolytes were prepared or obtained as indicated below:

Sample 1 illustrates a water-swellable water-insoluble ionic complex prepared by non-aqueous precipitation polymerization. Sample 17 illustrates a water-swellable, water-insoluble covalently crosslinked copolymer prepared by non-aqueous precipitation polymerization. Samples 19 and 21 illustrate commercially available water-soluble polymers. Sample 23 illustrates a commercially available water-insoluble, water-swellable graft copolymer. Sample 25 illustrates a commercially available water-swellable, water-insoluble covalently crosslinked copolymer. Samples 27, 29 and 31 illustrate water-soluble polymers formed by aqueous solution polymerization

| SAMPLES 1 and 17 (NON-AQUEOUS PRECIPITATION POLYMERIZATION) | | |
|---|---|---|
| Addition A | Sample 1 | Sample 17 |
| Methanol | 280 | 280 |
| Addition B | | |
| Acrylic Acid | 100 | 100 |
| Basic aluminum acetate | 2 | — |
| Potassium hydroxide | 50 | 50 |
| Methanol | 200 | 200 |
| Allyl methacrylate | 0.25 | — |
| N,N'-methylene bisacrylamide | — | 0.75 |
| Addition C | | |
| Methanol | 15 | 15 |
| t-butyl peroxypivalate | 0.35 | 0.35 |

Addition "A" was charged to three liter round bottom flask equipped with agitation, condenser, and heating bath. 25% of Addition "B" was added to the flask and the contents heated to reflux (68° C). Addition "C" was added uniformly over 2 hours. After some precipitation was observed, the remainder of Addition B was slowly and uniformly added over one hour. After a total reaction time of three hours, the product was cooled, filtered, washed and dried at 60° C, yielding a white polymer powder.

SAMPLES 19, 21, 23 AND 25 (USE OF COMMERCIAL POLYMERS)

CMC-7H is the tradename of Hercules, Inc. for a sodium carboxymethyl cellulose having a DS of 0.75 (Sample 19).

KELZAN is the tradename of Kelco Corp. for a polysaccharide derived from kelp (Sample 21).

SGP-502S is the tradename of General Mills, Inc. for a partially neutralized salt of a saponified starch/acrylonitrile graft copolymer (Sample 23).

DOW XD-1300 is the tradename of Dow Chemical Co. for a covalently crosslinked acrylic acid/acrylamide copolymer (Sample 25).

| SAMPLES 27, 29 AND 31 (AQUEOUS SOLUTION POLYMERIZATION) | |
|---|---|
| The monomers used in each sample were as follows: | |
| SAMPLE | MONOMERS (proportions, by weight) |
| 27 | Methacrylamide/methacrylic acid (50/50) |
| 29 | Hydroxethyl methacrylate/2-acrylamido-2-methyl propane sulfonic acid (50/50) |
| 31 | Acrylic acid |

2210 grams of water and 400 grams of total monomers were charged to a three liter round bottomed flask equipped with agitation, condenser, nitrogen purge and heating bath. The contents were agitated under nitrogen purge while heating to 70° C. At 70° C a solution of 50 grams of water and 0.80 grams of ammonium persulfate was uniformly added in increments over 30 minutes while maintaining 70° C. One hour past the addition, 0.40 grams of ammonium persulfate was added. After a total reaction time of 3.5 hours, the reaction was cooled. The final polymer product was dried and ground to a powder.

EXAMPLE II

To prepare Samples 2–16, 18, 20, 22, 24, 26, 28, 30 and 32, twenty grams of a dry absorbent composition of matter described in Example I were added to a 500 cc flask equipped with agitation, heating bath and condenser. Sixty grams of the dispersing medium indicated in Table I were added, followed by the addition of the polyvalent metal compound indicated in Table I. The mixture was agitated and heated to 68° C and held for 1 hour. The resultant dispersion was cooled and filtered, and the solid product was then dried for analysis.

EXAMPLE III

For each of Samples 1–32, a beaker containing 100 grams of water was agitated vigorously while 0.50 grams of the modified or unmodified dry absorbent composition of matter was quickly dumped in the beaker. The degree of initial dispersion (non-lumping) was recorded in Table I as was the time required for substantially complete dispersion (dispersion time). Initial power dispersion ratings were assigned as follows: excellent (no discernible lumping), very good (71–90% dispersion), good (51–70% dispersion), fair (41–50% dispersion), poor (21–40% dispersion), very poor (20% dispersion or less).

The dry absorbent compositions of matter modified by the surface treatment process of the present invention (Samples 2–16, 18, 20, 22, 24, 26, 28, 30 and 32) in each case exhibited greatly improved initial dispersion and a substantially reduced dispersion time relative to the corresponding unmodified dry absorbent compositions of matter (Samples 1, 17, 21, 23, 25, 27, 29 and 31, respectively).

has had an opportunity to enter into the particle interior where it acts to break-up the particle from within and thus reduce initial lumping as well as the time required to achieve full dispersion.

Now that the preferred embodiments of the present invention have been described, various modifications and improvements thereon will become readily apparent to those skilled in the art. Accordingly, the spirit and scope of the present invention is to be limited only by the appended claims, and not by the foregoing disclosure.

We claim:

1. A process for surface treating a water-absorbent composition of matter to improve its aqueous dispersibility comprising the steps of
    A. forming a dispersion comprising (i) a water-absorbent composition of matter based on an anionic poly-electrolyte, (ii) polyvalent, cations of at least one metal, and (iii) a dispersing medium in which said composition of matter is substantially insoluble;
    B. maintaining said dispersion at a temperature of about −40° to about +150° C for a period of time sufficient for said cations to ionically complex the outer surface of said composition of matter exposed to said dispersing medium; and
    C. removing said dispersing medium.

2. The process of claim 1 wherein said cations are

TABLE I

| Sample No. | Base Polymer Ex.I | Polyvalent Metal Compound | Dispersing Medium * | Cation Level ** | Initial Dispersion | Dispersion Time (Min.) |
|---|---|---|---|---|---|---|
| 1 | — | — | MeOH | — | v. poor | 15 |
| 2 | 1 | Basic Aluminum acetate | 90 MeOH/10 H$_2$O | 0.21 | v. good | 5 |
| 3 | 1 | " | " | 0.42 | v. good | 4 |
| 4 | 1 | " | 90 EtOH/10 H$_2$O | 0.42 | v. good | 4 |
| 5 | 1 | Chromium acetate | 90 MeOH/10 H$_2$O | 0.42 | excellent | 4 |
| 6 | 1 | Zirconium acetate | 41 | 0.42 | excellent | 4 |
| 7 | 1 | Zinc acetate | " | 3.48 | excellent | 1 |
| 8 | 1 | Aluminum octoate | " | 0.42 | good | 5 |
| 9 | 1 | Manganous acetyl acetate | Toluene | 0.64 | v. good | 5 |
| 10 | 1 | Cobaltous acetyl acetate | " | 0.64 | good | 5 |
| 11 | 1 | Barium acetate | 90 MeOH/10 H$_2$O | 0.42 | good | 10 |
| 12 | 1 | Aluminum isopropoxide | Toluene | 0.64 | good | 6 |
| 13 | 1 | Aluminum acetyl acetonate | Toluene | 1.08 | excellent | 1 |
| 14 | 1 | Stannous octoate | MeOH | 0.42 | good | 7 |
| 15 | 1 | Manganic acetyl acetonate | Hexane | 1.00 | v. good | 7 |
| 16 | 1 | Basic aluminum acetate | 80 dioxane/20 H$_2$O | 1.50 | excellent | 4 |
| 17 | — | — | — | — | v. poor | 16 |
| 18 | 17 | Basic aluminum acetate | 90 MeOH/10 H$_2$O | 0.64 | excellent | 6 |
| 19 | — | — | — | — | v. poor | >30 |
| 20 | 19 | Basic aluminum acetate | MeOH | 0.64 | excellent | 15 |
| 21 | — | — | — | — | v. poor | >30 |
| 22 | 21 | Basic aluminum acetate | MeOH | 0.64 | excellent | 5 |
| 23 | — | — | — | — | v. poor | >20 |
| 24 | 23 | Chromium acetate | MeOH | 0.30 | excellent | 5 |
| 25 | — | — | — | — | v. poor | 8 |
| 26 | 25 | Basic aluminum acetate | 90 MeOH/10 H$_2$O | 0.21 | excellent | 2 |
| 27 | — | — | — | — | v. poor | >15 |
| 28 | 27 | Basic aluminum acetate | MeOH | 0.86 | good | 15 |
| 29 | — | — | — | — | v. poor | >15 |
| 30 | 29 | Basic aluminum acetate | MeOH | 0.86 | good | 15 |
| 31 | — | — | — | — | v. poor | >15 |
| 32 | 31 | Zirconium acetate | MeOH | 0.64 | excellent | 8 |

* MeOH is methanol; ETOH is ethanol (ratios on a weight basis).
** Milliequivalents of cation per gram of absorbent composition matter on a dry basis.

To summarize, the aqueous dispersibility or wet-out of an absorbent composition of matter based on an anionic poly-electrolyte (of any of the classes described herein) is improved by a surface treatment process which ionically complexes the anionic poly-electrolyte chains with polyvalent metal cations. The modified particles of the composition have a greater linkage density on their surface than in their interior so that formation of a relatively water-impermeable gel on the particle surface after rapid exposure thereof to large quantities of aqueous fluid is delayed until the aqueous fluid selected from the group consisting of ions of the metals of Groups IIA–VIA, IB–VIIB, and VIII.

3. The process of claim 1 wherein about 0.05–10.0 milliequivalents of said cations are present in said dispersion per gram of said composition of matter on a dry basis.

4. The process of claim 3 wherein about 0.1–2.0 milliequivalents of said cations are present in said dispersion per gram of said composition of matter on a dry basis.

5. The process of claim 1 wherein said dispersing medium is selected from the group consisting of aliphatic and aromatic esters, ketones, alkyl ethers, alkanes containing 5-18 carbon atoms, aromatics, and blends of water-miscible solvents with water.

6. The process of claim 1 wherein said dispersion is maintained at said temperature for at least a minute.

7. The process of claim 6 wherein said dispersion is maintained at a temperature of about 25° C to 110° C for about 5-60 minutes.

8. The process of claim 1 wherein said cations are introduced as a metal compound ionizable in said dispersing medium.

9. The process of claim 1 wherein said composition of matter comprises a water-swellable, water-insoluble ionic complex of a water-soluble anionic poly-electrolyte and polyvalent metal cations having a valence of at least three.

10. The process claim 1 wherein said composition of matter comprises a water-swellable, water-insoluble covalently crosslinked anionic poly-electrolyte.

11. The process of claim 1 wherein said composition of matter comprises a water-insoluble anionic poly-electrolyte.

12. The process of claim 1 wherein about 0.5-100 parts of said dispersing medium are present in said dispersion per part by weight of said composition of matter on a dry basis.

13. The process of claim 12 wherein about 2-10 parts of said dispersion medium are present in said dispersion per part by weight of said composition of matter on a dry basis.

14. A water-absorbent composition of matter comprising water-dispersible water-absorbent particles based on an anionic poly-electrolyte, each of said particles having a linkage density at the particle surface greater than the linkage density in the particle interior, the linkages at the particle surface comprising at least in part ionic complexing of said anionic poly-electrolyte by polyvalent metal cations.

15. The composition of matter of claim 14 wherein said cations are selected from the group consisting of ions of the metals of Groups IIA-VIA, IB-VIIB, and VIII.

16. The composition of matter of claim 14 wherein said particles comprise about 0.05-10.0 milliequivalents of said cations per gram of said composition of matter on a dry basis.

17. The composition of matter of claim 14 wherein said particle interior comprises a water-swellable, water-insoluble ionic complex of a water-soluble anionic poly-electrolyte and a polyvalent metal cation having a valence of at least three.

18. The composition of matter of claim 14 wherein said particle interior comprises a water-swellable, water-insoluble covalently crosslinked anionic poly-electrolyte.

19. The composition of matter of claim 14 wherein said particle interior comprises a water-soluble anionic poly-electrolyte.

* * * * *